United States Patent [19]

York et al.

[11] Patent Number: 5,696,091
[45] Date of Patent: Dec. 9, 1997

[54] USE OF GROWTH FACTOR AND ANTIMETABOLITE COMBINATION TO PREVENT OR RETARD SECONDARY CATARACT FORMATION

[75] Inventors: Billie M. York; Jon C. Nixon, both of Fort Worth; Karen C. Sams, Arlington, all of Tex.

[73] Assignee: Alcon Laboratories, Inc., Fort Worth, Tex.

[21] Appl. No.: 602,476

[22] Filed: Feb. 20, 1996

Related U.S. Application Data

[63] Continuation of Ser. No. 128,629, Sep. 29, 1993, abandoned.
[51] Int. Cl.$^6$ .............................. A61K 38/00; A61F 2/00
[52] U.S. Cl. .............................. 517/12; 514/21; 514/912; 514/913; 530/399; 424/427; 604/49
[58] Field of Search .............................. 514/12, 21, 912, 514/913; 530/399; 424/427; 604/49

[56] References Cited

U.S. PATENT DOCUMENTS

| | | | |
|---|---|---|---|
| 4,717,717 | 1/1988 | Finkenaur | 514/21 |
| 4,863,902 | 9/1989 | Amagase et al. | 514/12 |
| 4,962,091 | 10/1990 | Eppstein et al. | 514/2 |
| 4,966,577 | 10/1990 | Crosson et al. | 604/20 |
| 5,055,291 | 10/1991 | Lam et al. | 424/85.91 |
| 5,061,786 | 10/1991 | Burnier et al. | 530/326 |
| 5,108,989 | 4/1992 | Amento et al. | 514/12 |
| 5,124,392 | 6/1992 | Robertson et al. | 524/427 |

FOREIGN PATENT DOCUMENTS

| | | |
|---|---|---|
| A-0433225 | 6/1991 | European Pat. Off. |
| WO 92/15614 | 9/1992 | WIPO |
| WO 93/19769 | 10/1993 | WIPO |
| WO 94/01124 | 1/1994 | WIPO |

OTHER PUBLICATIONS

Schrier et al, *Research in Experimental Medicine,* vol. 193, No. 4, pp. 195–205, 1993.
Schultz et al., *Acta Ophthalmologica,* vol. 70, No. S202, pp. 60–66, 1992.
Glaser et al, *Ophthalmology,* vol. 99, No. 7, pp. 1162–1173, 1992.
Smiddy et al, *Archives of Ophthalmology,* vol. 107, No. 1, pp. 557–580, 1989.
Connor J., T.B., et al., "Correlation of Fibrosis and Transforming Growth Factor—β Type 2 Levels in the Eye", *The American Society for Clinical Investigations, Inc.,* vol. 83, pp 1661–1666 (May 1989).
Tripathi, R.C., et al., "Growth Factors in the Aqueous Humor and Their Therapeutic Implications in Glaucoma and Anterior Segment Disorders of the Human Eye", *Drug Development Research,* 22, 1991 Wiley-Liss, Inc. pp.1–23.
Yaldo, M. K., et al., "Long–term Effects of Mitomycin on Filtering Blebs: Lack of Fibrovascular Proliferative Response following severe inflammation", *Arch. Ophthalmol.* vol. 111, No. 6, pp. 824–826 (Jun. 1993).

Mermoud, A., et al., "Surgical Management of Post–Traumatic Angle Recession Glaucoma", *Ophthalmology,* vol. 100, No. 5, pp. 634–642 (1993).
Costa, V.P., et al., "Wound Healing Modulation in Glaucoma Filtration Surgery", *Ophthalmic Surgery,* vol. 24, No. 3, pp. 152–170 (Mar. 1993).
Joseph, J.P., et al., "Wound Healing as a Barrier to Successful Filtration Surgery", *Eye,* 2 Supl., pp. 113–123 (1988).
Glaser, B., et al., "Transforming Growth Factor–$\beta_2$ for the Treatment of Full–thickness Macular Holes", *Ophthalmology,* vol. 99, No. 7, pp. 1162–1173 (1992).
Smiddy, W., et al., "Transformin Growth Factor Beta", *Archives of Ophthalmology,* vol. 107, No. 1, pp. 577–580 (1989).
Glaser, B., et al., "Induction of a 'Retinal Patch' By Transforming Growth Factor–Beta in the Treatment of Full Thickness Macular Holes", *Investigative Ophthalmology & Visual Science,* vol. 32, No. 4, p. 713 (Mar. 1991).
S. J. Ryan Chief Editor, "Retina", Chapter 68, published 1989 by the C. V. Mosby Company (St. Louis), pp. 229–242.
T. Schreier, et al., "Fibroblast migration and proliferation during in vitro wound healing. A quantitative comparison between various growth factors and a low molecular weight blood dialyzate used in the clinic to normalize impaired wound healing", *Research In Experimental Medicine,* vol. 193, No. 4, pp. 195–205 (1993).
Takahashi, N., et al., "The Cytotoxic Effect Of 5–Fluorouracil On Cultured Human Conjunctival Cells", *Lens And Eye Toxicity Research,* vol. 6, Nos. 1 & 2, pp. 157–166 (1989).
Hendriks, T., et al., "Inhibition of basal and TGFβ–induced fibroblast collagen synthesis by antineoplastic agents. Implications for wound healing", *British Journal of Cancer,* vol. 67, No. 3, pp. 545–550 (Mar. 1993).
Shah, et al., "Control of scarring in adult wounds by neutralsing antibody to transforming growth factor β", *The Lancet,* vol. 339, pp. 213–214 (1992).
Whitby, et al, "Immunohistochemical Localization of Growth Factors in Fetal Wound Healing", *Develomental Biology,* vol. 147, pp. 207–215 (1991).

(List continued on next page.)

*Primary Examiner*—Cecilia J. Tsang
*Assistant Examiner*—Abdel A. Mohamed
*Attorney, Agent, or Firm*—Gregg C. Brown

[57] ABSTRACT

The intraocular use of combinations of lens epithelial cell growth stimulators (e.g., TGF-β) and antimetabolites (e.g., mitomycin C) is described. The combination is applied to the capsular bag to prevent or retard the formation of secondary cataracts following cataract surgery. The lens epithelial cell stimulators activate DNA synthesis in dormant lens epithelial cells, and thereby make those cells susceptible to the anti-metabolites. This enables the antimetabolites to suppress the proliferation of lens epithelial cells to a much greater extent, relative to the proliferation observed when the metabolites alone are utilized. The increased suppression of the growth of lens epithelial cells results in a significant improvement in the ability to prevent or retard the formation of opacities on the lens capsule (i.e., secondary cataracts).

12 Claims, 1 Drawing Shee

OTHER PUBLICATIONS

Levine, et al., "Spatial and Temporal Patterns of Immunoreactive Transofrming Growth Factor $\beta_1$, $\beta_2$, and $\beta_3$ during Excisional Wound Repair", *American Journal of Pathology*, vol. 143, No. 2, pp. 368–380 (Aug. 1993).

Schultz, et al., "Effects Of Growth Factors On Corneal Wound Healing", *Acta Ophthalmologica*, vol. 70, No. S202, pp. 60–66 (1992).

Nishida, et al. "Immunohistochemical locatization of transforming growth factor–beta 1, –beta 2, and –beta 3 latency–associated peptide in human cornea", Abstract 94321139, Database Medline (1994). t

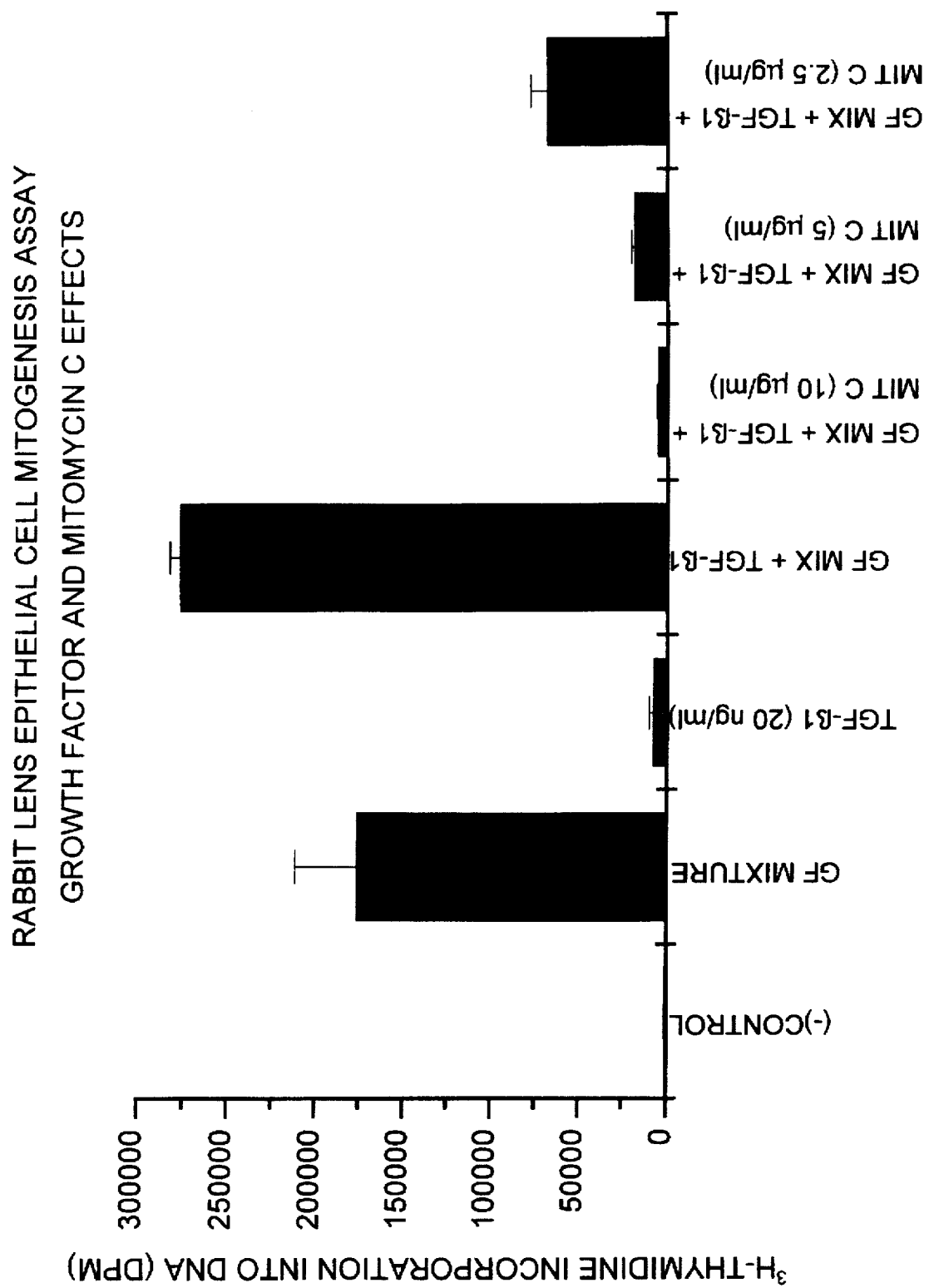

USE OF GROWTH FACTOR AND ANTIMETABOLITE COMBINATION TO PREVENT OR RETARD SECONDARY CATARACT FORMATION

This is a continuation of application Ser. No. 08/128,629, filed Sep. 29, 1993, now abandoned.

BACKGROUND OF THE INVENTION

The present invention relates to the field of ophthalmology. More specifically, the invention relates to the field of cataract surgery, wherein the natural crystallin lens of the human eye is surgically removed and an artificial lens is implanted.

Modern cataract surgery typically involves implantation of an artificial lens, referred to as an "intraocular lens" or "IOL", in the posterior chamber of the eye. The preferred site of implantation is within the capsule which surrounds the natural crystallin lens. When the natural crystallin lens is surgically removed, a portion of the anterior face of the lens capsule is also removed. This provides an opening which allows the artificial lens to be placed within the remaining portion of the lens capsule, which is also referred to as the "capsular bag". The capsular bag is considered to be the ideal location for implantation of an intraocular lens. Unfortunately, there is a significant problem associated with implantation of intraocular lenses in the capsular bag.

The capsular bag is normally cleaned or "polished" by the ophthalmic surgeon to remove lens epithelial cells and other tissue remnants. This helps to ensure that deposits in the lens capsule do not impair the vision of the patient. However, it is generally not possible for the surgeon to remove all of the lens epithelial cells, particularly in the outer perimeter of the capsular bag. The remaining lens epithelial cells may eventually cause opacifications which impair the vision of the patient. Such impairment is referred to as "secondary cataract". The formation of a secondary cataract may require further medical treatment, such as use of a YAG laser to break up the opacifications, or further surgery.

In the past, the use of antimetabolites, such as 5'-fluorouracil or mitomycin C, has been suggested as a means of preventing secondary cataract formation. Although antimetabolites can prevent the growth and proliferation of active lens epithelial cells, this approach has not proved to be effective. It is believed that the effectiveness of antimetabolites in preventing lens epithelial cell growth is severely limited by the fact that these agents only target cells that are actively dividing. Since the antimetabolites are normally applied to the lens capsule in a single dose at the time of surgery, it is not possible for these agents to prevent the subsequent proliferation of lens epithelial cells which are dormant (i.e., not actively dividing) at the time of surgery. A significant number of lens epithelial cells may therefore evade the action of the antimetabolite and proliferate at a later time. This lens epithelial cell proliferation ultimately contributes to the formation of lens opacifications or secondary cataracts.

Thus, there is a need for an improved method of preventing or retarding the formation of secondary cataracts. The present invention is directed to satisfying this need.

SUMMARY OF THE INVENTION

The present invention provides an improved method of preventing or retarding secondary cataract formation. The method is based on the application of a composition which contains a combination of one or more lens epithelial cell growth stimulators and an antimetabolite to the lens capsule at the time of surgery. Various lens epithelial cell growth stimulators or combinations thereof may be utilized for this purpose, but the most preferred approach is to utilize a combination which includes transforming growth factor-beta ("TGF-$\beta$"). The lens epithelial cell stimulator component of the composition stimulates lens epithelial cells which are dormant at the time of surgery, so as to cause these cells to initiate DNA synthesis. This mitogenic activation of the lens epithelial cells enhances their susceptability to the action of the antimetabolite component of the composition.

The above-described method results in a much greater suppression of lens epithelial cell growth, compared to that achieved with an antimetabolite alone. As a result, the method provides a significant improvement in the ability to prevent or retard the formation of secondary cataracts.

BRIEF DESCRIPTION OF THE DRAWINGS

FIG. 1, the sole figure of drawings, is a bar graph presentation of the data discussed in Example 1.

DESCRIPTION OF PREFERRED EMBODIMENTS

The lens epithelial cell stimulators which may be utilized in the present invention include all agents which will activate dormant lens epithelial cells by stimulating the initiation of DNA synthesis. Such agents are collectively referred to herein as "lens epithelial cell growth stimulators". The use of mixtures which include various isoforms of TGF-$\beta$, and modifications thereof, is preferred.

There are five known isoforms of TGF-$\beta$. These forms have been designated as TGF-$\beta_1$, TGF-$\beta_2$, TGF-$\beta_3$, TGF-$\beta_4$ and TGF-$\beta_5$, the first three being common to man. The physical properties of these growth factors, sources of same, and methods of purification are known. See, for example, U.S. Pat. No. 5,108,989 (Amento, et al; Genentech, Inc.) and the references cited therein at lines 21–45 of column 1. The entire contents of that patent relating to the various forms of TGF-$\beta$ are hereby incorporated by reference in the present specification. As utilized herein, the term "TGF-$\beta$" encompasses one or more polypeptides having lens epithelial cell stimulating activity, such as mature and precursor forms of TGF-$\beta_1$, TGF-$\beta_2$, TGF-$\beta_3$, TGF-$\beta_4$ and TGF-$\beta_5$; hybrid TGF-$\beta$s; latent TGF-$\beta$ complexes; TGF-$\beta$ analogs (e.g., deletion variants and hybrids); and biologically active polypeptides based on transforming growth factor-beta sequences, such as those described in U.S. Pat. No. 5,061,786 (Burnier, et al.; Genentech, Inc.).

The lens epithelial cell growth stimulators which may be utilized in the present invention also include transforming growth factor-alpha (TGF-$\alpha$), keratinocyte growth factor (KGF), epidermal growth factor (EGF), platelet-derived growth factors (PDGF-BB, -AA, or -AB), basic fibroblast growth factor (b-FGF), acid fibroblast growth factor (a-FGF), angiogenin, nerve growth factor (NGF), insulin-like growth factor I and II (IGF-I and IGF-II), and other proteins or polypeptides having mitogenic activity relative to lens epithelial cells. As used herein, the term "polypeptides" encompasses natural, synthetic and recombinant polypeptides, including polypeptides having deleted, replaced or altered amino acid sequences in comparison with the full-length natural polypeptide or biologically active fragments thereof.

The lens epithelial cell growth stimulators utilized in the present invention are preferably human derived. As used herein, the term "human derived" encompasses agents recovered from human tissues and agents produced from human cell lines by means of recombinant DNA technology.

The most preferred lens epithelial cell growth stimulator of the present invention is a mixture which includes TGF-β, in combination with EGF, b-FGF, TGF-α and PDGF-BB.

The compositions utilized in the present invention contain one or more of the above-described lens epithelial cell stimulators in an amount sufficient to achieve mitogenic activation of dormant lens epithelial cells. The amount of lens epithelial cell stimulator required for this purpose will vary depending on the particular agent(s) utilized, but will generally be from about 0.01 to about 10,000 nanograms/milliliter ("ng/ml").

The compositions utilized in the present invention will also include one or more antimetabolites to suppress the proliferation of lens epithelial cells. Various antimetabolites may be utilized for this purpose. The antimetabolites which may be utilized can be generally characterized as being structural analogs to metabolically active molecules, such as purines, pyrimidines and folic acid. These compounds interfere with normal DNA/RNA synthesis, and thereby terminate cell growth. The net effects of this action are reduced mitotic activity and impaired proliferation of lens epithelial cells. Examples of antimetabolites which may be utilized in the present invention include mitomycin C, 5'-fluorouracil, arabinocytosine, taxol, actinomycin C and methotrexate. The use of mitomycin C as the antimetabolite component of the present invention is preferred, because it is relatively less toxic to corneal endothelial cells than other antimetabolites, such as 5'-fluorouracil.

The compositions utilized in the present invention contain one or more of the above-described antimetabolites in an amount sufficient to suppress the growth of lens epithelial cells. The amount of antimetabolite required for this purpose will vary depending on the particular antimetabolite(s) selected, but will generally be from about 0.01 to about 500 micrograms/milliliter ("mcg/ml").

The above-described combinations of lens epithelial cell stimulators and antimetabolites can be included in various types of pharmaceutical vehicles suitable for intraocular use. The vehicles are preferably aqueous, and are formulated so as to be chemically and physically compatible with ophthalmic tissues. For example, viscoelastic formulations currently utilized in connection with intraocular surgical procedures, such as HEALON® (sodium hyaluronate) (Kabi Pharmaci Ophthalmics Inc.) or VISCOAT® (sodium chondrotin sulfate-sodium hyaluronate) Sterile Ophthalmic Viscoelastic (Alcon Laboratories, Inc.) (Alcon Surgical, Inc.) may be utilized as a vehicle for the above-described combinations of growth factors and antimetabolites. Such viscous formulations are coherent and tend to adhere to tissue. These properties help to ensure that the compositions will expose lens epithelial cells to the actions of the growth factor/antimetabolite combinations of the present invention. This is particularly true when the compositions are applied following removal of the natural crystallin lens, since at that point the capsular bag will be at least partially open and therefore prone to immediately losing any fluid which is applied to the interior of the bag by means of irrigation. The use of a viscous solution or semi-solid composition may therefore be preferable in some cases.

In other cases, such as those where the growth factor/antimetabolite combination is injected into the capsular bag prior to removal of the natural crystallin lens, the viscosity of the composition will not be a primary concern, since leakage of the composition from the capsular bag will be a less significant problem. The use of an aqueous solution as the vehicle for the growth factor/antimetabolite combination may therefore be preferred in such cases. The aqueous solutions which might be utilized must be compatible with intraocular tissues, and should preferably help to maintain the integrity and function of intraocular tissues during the surgical procedure. The aqueous solutions which might be utilized for the above-described purposes include balanced saline solutions, such as BSS® Balanced Salt Solution and BSS Plus® Balanced Salt Solution Enriched with Bicarbonate, Dextrose and Glutathione, both of which are available from Alcon Surgical, Inc., and BION™ Tears Lubricant Eye Drops (Alcon Laboratories, Inc.), which is available from Alcon Laboratories, Inc., Fort Worth, Tex.

As will be appreciated by those skilled in the art, the above-described compositions must be sterile and should not include any agents (e.g., antimicrobial preservatives) which will be toxic to sensitive intraocular tissues, particularly corneal endothelial cells. The above-described compositions can be formulated in accordance with techniques known to those skilled in the art. The following publications may be referred to for further details concerning the formulation of compositions containing polypeptides, such as TGF-β: U.S. Pat. No. 4,717,717 (Finkenaur; Ethicon, Inc.); U.S. Pat. No. 4,962,091 (Eppstein, et al.; Syntex (U.S.A.) Inc.); and WO 92/15614 (Takruri; Chiron Ophthalmics, Inc.); and references cited in the foregoing patent publications.

The above-described compositions can be applied to the lens capsule by means of various techniques. For example, the compositions can be applied to the interior of the capsular bag by means of a syringe following removal of the crystallin lens, or can be injected into the lens capsule prior to removal of the crystallin lens by means of phacoemulsification or other methods. The only critical requirement with respect to how the compositions are applied is that the compositions be distributed throughout the lens capsule, and remain in contact with the dormant lens epithelial cells for a length of time sufficient to achieve mitogenic activation of those cells. The amount of time required to achieve this purpose will vary somewhat depending on circumstances such as the lens epithelial cell stimulators and antimetabolites utilized, and the method by which the lens epithelial cell stimulator/antimetabolite combination is applied to the capsular bag (i.e., injection prior to phacoemulsification or irrigation following cataract removal). However, the compositions will generally need to remain in contact with the interior of the capsular bag for approximately five to ten minutes or longer. The compositions may be removed by means of conventional irrigation and aspiration techniques.

The following example is provided to illustrate the effect of the above-described lens epithelial cell stimulators and antimetabolites on lens epithelial cells.

EXAMPLE 1

Studies were conducted to examine the effects of a particular antimetabolite, mitomycin C, on the mitogenic capability of cultured rabbit lens epithelial cells. A standard in vitro mitogenesis assay was utilized for these experiments. Normal rabbit lens epithelial cells (designation AG04676 from the Coriell Institute for Medical Research Cell Repository) between passage number six and thirteen were plated in a 96-well tissue culture plate. The cells were fed fresh MEM Eagle medium with Earle's salts supplemented with 10% normal rabbit serum, 2 mM 1-glutamine, and 0.05 mg/ml gentamicin every three to four days until the cells were approximately 80% confluent. The experiment was initiated three to five days after the last medium replacement to assure that the cells were at their maximum mitogenic potential.

The test compounds (growth factor mixture and antimetabolite), formulated in serum-free culture medium, were exposed to cells in triplicate wells for ten minutes. The test substances were then aspirated off of the cells and replaced by serum-free culture medium. After an eighteen hour incubation, tritiated thymidine was exposed to the cells for six hours. The DNA was then precipitated with trichloroacetic acid; thymidine not incorporated into DNA was removed by washing, and the labeled DNA was solubilized with sodium dodecyl sulfate. The tritiated thymidine which was incorporated into the DNA of actively dividing cells was quantitated using a beta scintillation counter, and the mean and standard deviation were calculated for the triplicate sets.

In these particular studies, a mixture of growth factors was used to maximally stimulate mitogenesis in these cells. The mixture consisted of 30 ng/ml of epidermal growth factor and 20 ng/ml each of platelet-derived growth factor (-BB homodimer), basic fibroblast growth factor, and transforming growth factor-alpha. As depicted in FIG. 1, the addition of 20 ng/ml of transforming growth factor-beta significantly increased the stimulatory capability of the growth factor mixture. Mitomycin C was added to the cells in the presence of the growth factor mixture at various concentrations.

The results presented in FIG. 1 indicate that the cells exposed to the growth factor mixture were more active in synthesizing DNA, when compared to control (i.e., unstimulated) cells. In addition, TGF-$\beta_1$ by itself has little or no effect on cell growth; however, when added to the growth factor mixture, TGF-$\beta_1$ enhances the DNA synthesis stimulatory effect. The mitogenic mixture which included TGF-$\beta_1$ maximized the stimulation of lens epithelial cell DNA synthesis. This stimulatory effect was effectively inhibited by mitomycin C (MIT C) at concentrations above 2.5 ug/ml (inhibition=75.5%). It is important to note that the growth factor mixture and mitomycin C were only exposed to the cells for a ten minute period.

What is claimed is:

1. A method of reducing the formation of secondary cataracts following extracapsular cataract surgery, which comprises applying to the interior of the capsular bag of an eye at the time of surgery a composition comprising a lens epithelial cell growth stimulator in an amount sufficient to activate dormant lens epithelial cells by stimulating the initiation of DNA synthesis, an antimetabolite in an amount sufficient to suppress the proliferation of lens epithelial cells, and a pharmaceutically acceptable vehicle therefor; wherein the use of the antimetabolite in combination with the lens epithelial cell growth stimulator suppresses the growth of lens epithelial cells in the posterior capsule to a greater extent than possible with the same dose of the antimetabolite when utilized alone.

2. A method according to claim 1, wherein the lens epithelial cell growth stimulator comprises TGF-$\beta$.

3. A method according to claim 1, wherein the composition is applied to the capsular bag by means of injection into the capsular bag prior to surgical removal of the lens.

4. A method according to claim 1, wherein the composition is applied to the capsular bag by means of irrigation following removal of the lens.

5. A method according to claim 1, wherein the composition comprises 0.01 to 10,000 ng/ml of the lens epithelial cell growth stimulator and 0.01 to 500 mcg/ml of the antimetabolite.

6. A method according to claim 1, wherein the lens epithelial cell growth stimulator comprises a growth factor.

7. A method according to claim 2, wherein the growth factor is human derived.

8. A method according to claim 1, wherein the antimetabolite is selected from the group consisting mitomycin C, 5'-fluorouracil, arabinocytosine, taxol, actinomycin C, and methotrexate.

9. A method according to claim 8, wherein the antimetabolite comprises mitomycin C.

10. A method according to claim 1, wherein the lens epithelial cell growth stimulator comprises a mixture of growth factors which includes TGF-$\beta$.

11. A method according to claim 10, wherein the mixture comprises TGF-$\beta_1$.

12. A method according to claim 11, wherein the mixture comprises TGF-$\beta_1$ in combination with EGF, b-FGF, TGF-$\alpha$ and PDGF-BB.

* * * * *